United States Patent [19]

Schiavone, Jr. et al.

[11] Patent Number: 5,171,386

[45] Date of Patent: Dec. 15, 1992

[54] MACHINE AND METHOD FOR THE AUTOMATED MANUFACTURE OF PROTECTIVE SPECTACLES

[75] Inventors: Michael C. Schiavone, Jr., Lancaster; James E. Beck; W. John Gaudlip, both of Mount Joy, all of Pa.

[73] Assignees: W. Peter Knepp; Christine F. Knepp, both of York, Pa.

[21] Appl. No.: 739,302

[22] Filed: Aug. 1, 1991

[51] Int. Cl.$^5$ ........................ B32B 31/16; B32B 31/00
[52] U.S. Cl. .................................. 156/73.1; 156/250; 156/256; 156/263; 156/264; 156/265; 156/494; 156/495; 156/510; 156/511; 156/516; 156/517; 156/556; 156/580.1; 264/23; 425/174.2
[58] Field of Search ............... 156/73.1, 73.4, 250, 156/256, 263, 494, 495, 556, 557, 559, 580.1, 261, 264, 265, 510, 511, 516, 517; 351/44, 178; 264/23; 425/174.2

[56] References Cited

U.S. PATENT DOCUMENTS

| | | | |
|---|---|---|---|
| 2,426,266 | 8/1947 | Haas | 351/44 X |
| 2,527,027 | 11/1950 | Mull | 351/44 X |
| 2,719,565 | 10/1955 | Wolff | 156/250 X |
| 2,759,519 | 8/1956 | Wolff | 351/178 X |
| 3,975,474 | 8/1976 | Leblanc | 264/23 |
| 4,668,316 | 5/1987 | Sager | 156/73.1 |
| 4,713,131 | 12/1987 | Obeda | 156/73.1 |

Primary Examiner—David A. Simmons
Assistant Examiner—J. Sells
Attorney, Agent, or Firm—Samuel M. Learned, Jr.

[57] ABSTRACT

A machine and method for the fully automated manufacture, assembly, and packaged delivery of protective spectacles of that type typically provided by an optometrist to a patient for temporary protective eyewear use following mydriatic eye examination procedures.

5 Claims, 5 Drawing Sheets

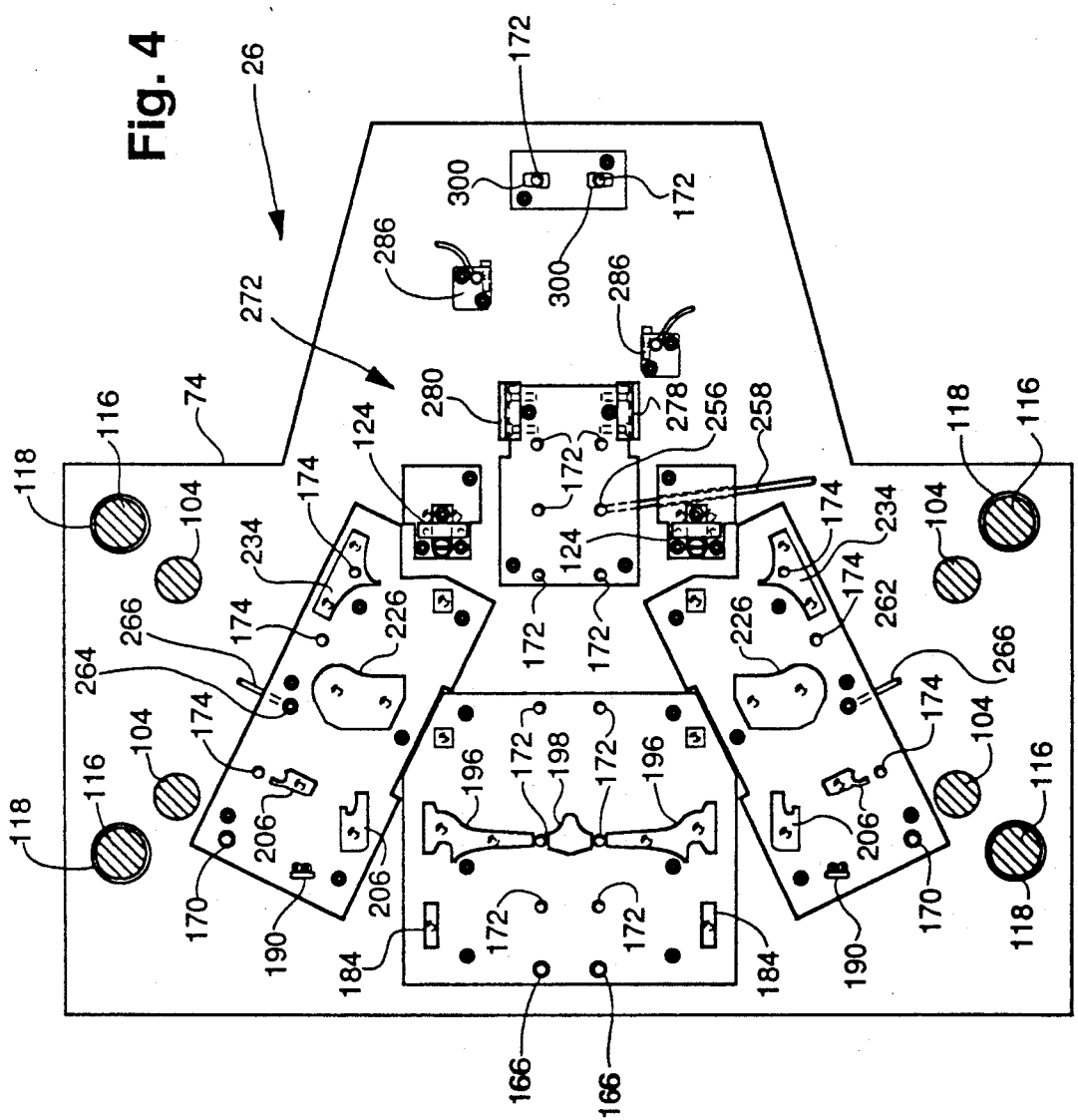

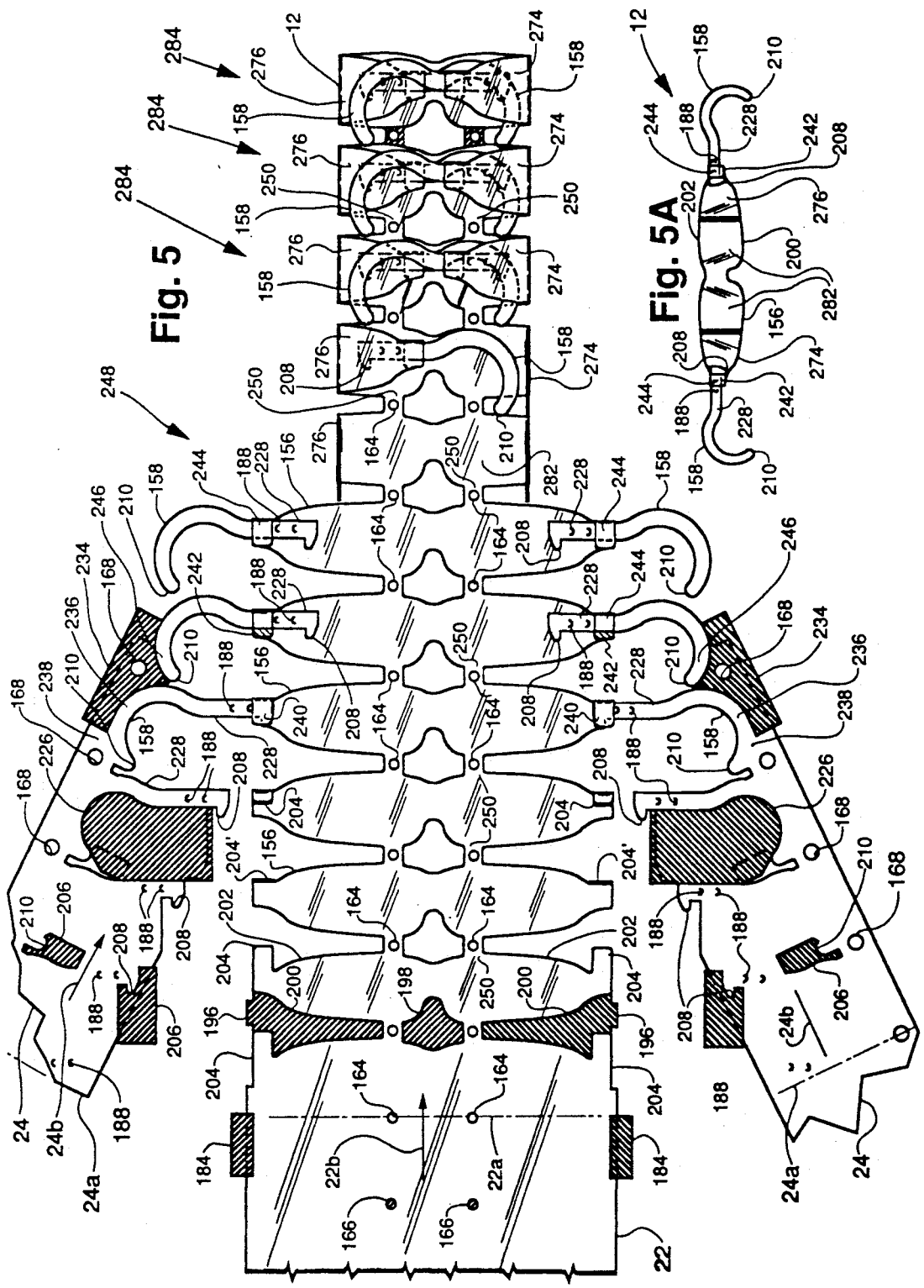

MACHINE AND METHOD FOR THE AUTOMATED MANUFACTURE OF PROTECTIVE SPECTACLES

BACKGROUND OF THE INVENTION

The present invention relates to a machine and method for accomplishing the automated manufacture, assembly and packaged delivery of protective spectacles such as those typically provided by an optometrist to a patient for temporary protective eyewear use following pupil dilative eye examination procedures, the type of protective eyewear device being commonly referred to as post-mydriatic spectacles and generally similar to those as disclosed and taught by Mull in U.S. Pat. No. 2,527,027 dated Oct. 24, 1950.

The traditional method for manufacturing post-mydriatic spectacles of the type referred to has, up until the present, been accomplished by a combination of separate mechanical die cutting and manual assembly and envelope packaging operations. And, up until recent times, although the labor contributive cost factors for the type of manufacturing operations employed have been a consideration, they have not been controlling. Since, however, the post-mydriatic spectacles of the type with which we are herein concerned are intended as a "give-away" item, and because the current manufacturing operations employed to make, assemble and package them are labor intensive, with the continuing escalation of both labor and material costs it has become no longer economically feasible to make and provide the subject post-mydriatic spectacles as a "give-away" item in a market environment and tradition where it continues to be expected. Thus, the need and incentive to provide a more efficient and economical manufacturing means and method for producing and packaging "give-away" post-mydriatic spectacles is timely, and met by the applicant's present invention as herein set forth describing in detail a machine and method for the automated manufacture of protective spectacles.

SUMMARY OF THE INVENTION

It is the principal object of the present invention to provide a machine for the auomated production and packaged delivery output of protective spectacles of that type typically provided by an optometrist to a patient for temporary protective eye wear use following pupil dilative eye examination procedures, the type of protective eyewear device hereby produced being commonly referred to as post-mydriatic spectacles.

It is also an object of the present invention to provide a machine that will automatically produce protective spectacles made from a flexible sheet material, which spectacles are provided with adjustable temples in order that they may be made to accommodate various sizes.

It is yet another object of the present invention to provide a machine for the automated manufacture of protective spectacles which is capable of substantially higher assembled and packaged spectacle production output per man hour than is otherwise currently possible with presently available equipment.

It is still another object of the instant invention to provide a machine for the automated manufacture of protective spectacles which is safe and relatively simple in operation, as well as a machine which requires a minimum of make-ready time, in addition to a machine which may be easily maintained, and set and operated by an employee not possessed of special skill or training.

It is another object of the present invention to provide a highly efficient automated production method for protective spectacle manufacture by embodying operational procedures which enable the accomplishment of simultaneous machine processing functions respectively upon the various component input materials for thereby achieving the automated assembly and packaged production output of finished protective spectacle product.

A further object of the present invention is to provide a machine and method for automated manufacture of protective spectacles which mechanically consolidates functions that have heretofore been relatively time consuming and separate mechanically and manually accomplished operations.

Details of the foregoing objects and of the invention, as well as other objects thereof, are set forth in the following specification and illustrated in the accompanying drawings comprising a part thereof.

BRIEF DESCRIPTION OF THE DRAWINGS

FIG. 4 is a bottom plan view of the punch holder section of said machine as shown in FIG. 2 and seen along the line 4—4 thereof.

FIG. 5 is a top plan view illustrating the progressive formation and automated machine assembly of the protective spectacle product sequentially made from the respective input material webs.

FIG. 5A is a front elevation view of a completed protective spectacle shown in a flat unfolded configuration to more clearly illustrate the component parts and assembly relationships respectively thereof.

DETAILED DESCRIPTION OF THE INVENTION

Figure 1:
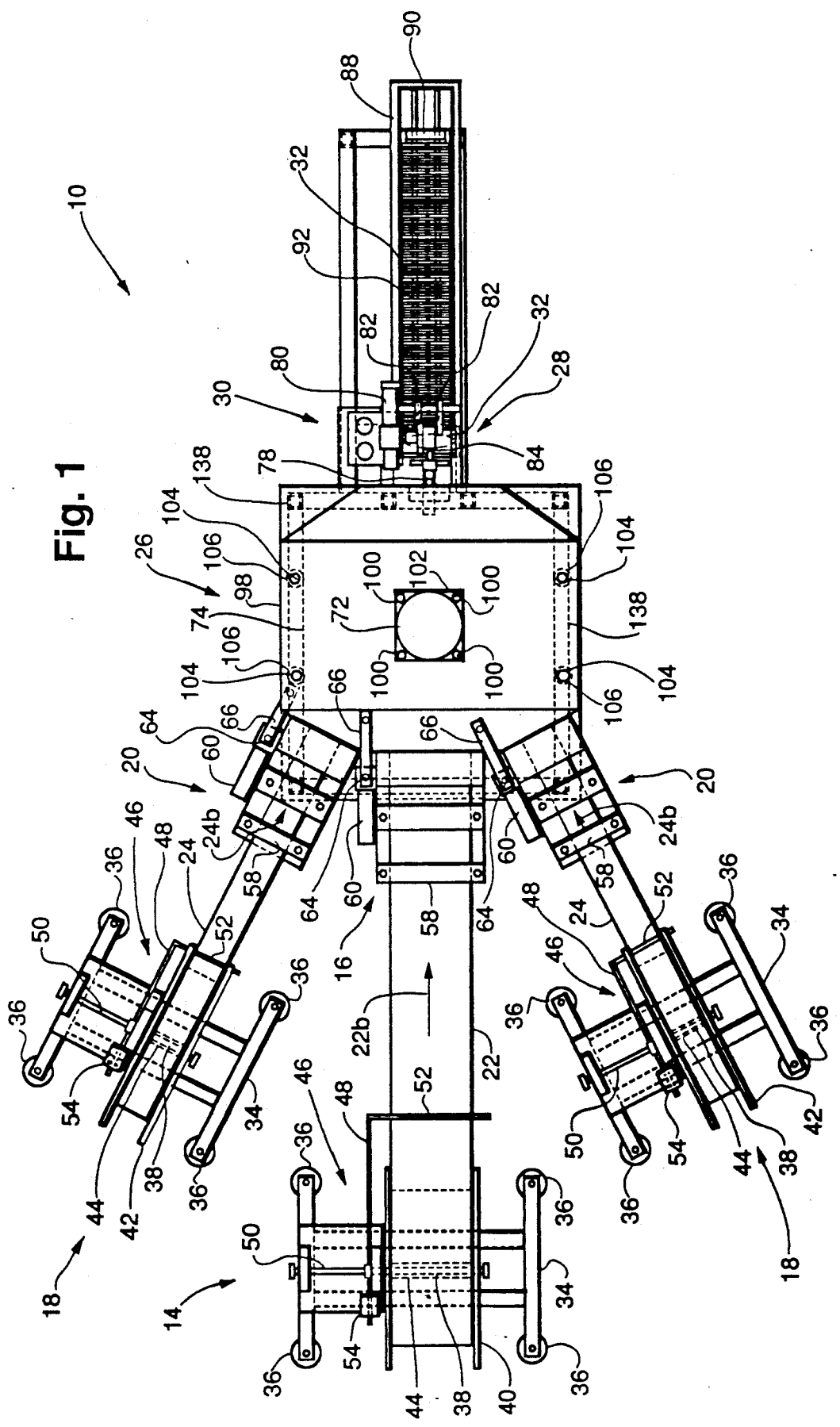
FIG. 1 is a top plan view of the machine embodying the principles and features of the present invention.

Referring to FIG. 1, the machine 10 of instant invention for the automated manufacture of protective spectacles 12, and the major mechanically integrated components of said machine 10 comprising the same are shown in a top plan view thereof, which components consist of a lens material infeed roll stand 14 and the lens material web indexing infeed 16 therefor, in addition to a set of temple material infeed roll stands 18 each having a temple material web indexing infeed 20 respectively therefor, the foregoing in turn respectively delivering the lens material web 22 and temple material webs 24 to the infeed material die punch and product assembly station 26 which with each operational cycle of said machine 10 concurrently completes a sequentially progressive plurality of product component parts formation and joining and assembly steps for delivery of a completed protective spectacle 12, and by means of the product pick-up and delivery station 28 removes and presents the completed protective spectacle 12 to the packaging station 30 for automated individual insertion of the same into a protective envelope 32, thereafter followed by delivery of the envelope packaged product to cartoning for shipping or storage.

Referring again to FIG. 1 to explain in greater detail both the major mechanical components of said machine 10 as well as the sequential method provided thereby for the automated formation, assembly, delivery and packaging of completed spectacles 12. The material infeed roll stands 14 and 18 respectively for the lens material web 22 and temple material webs 24 are of conventional design and structure for such devices, each being provided with a material infeed roll support frame 34 comprised of interconnected vertical and horizontal members and having adjustable foot pads 36 for operationally levelling the frame 34 at a machine 10 installation site, wherein each such frame 34 has an axle 38 which is adapted to insertably engage and support the lens material infeed roll 40 and temple material rolls 42 through the central reel core openings 44 respectively thereof. Each material infeed roll stand 14 and 18 is also provided with a web tensioner 46 which is comprised of a freely rotating counterbalance arm 48 attached to a rotating shaft 50 and having a web tensioning roller 52 at one end to ride on the material infeed web 22 or 24 and thereby dynamically maintain the same in a state of operationally balanced slack and tensioning during machine 10 running, and at the other end of said arm 48 having a slidably adjustable and set counterbalance weight 54 to accommodate roller 52 adjustment to the running characteristics of different web materials as well as ambient operational condition effects such as temperature and humidity upon the web materials and machine 10 running speed variations.

Figure 2:
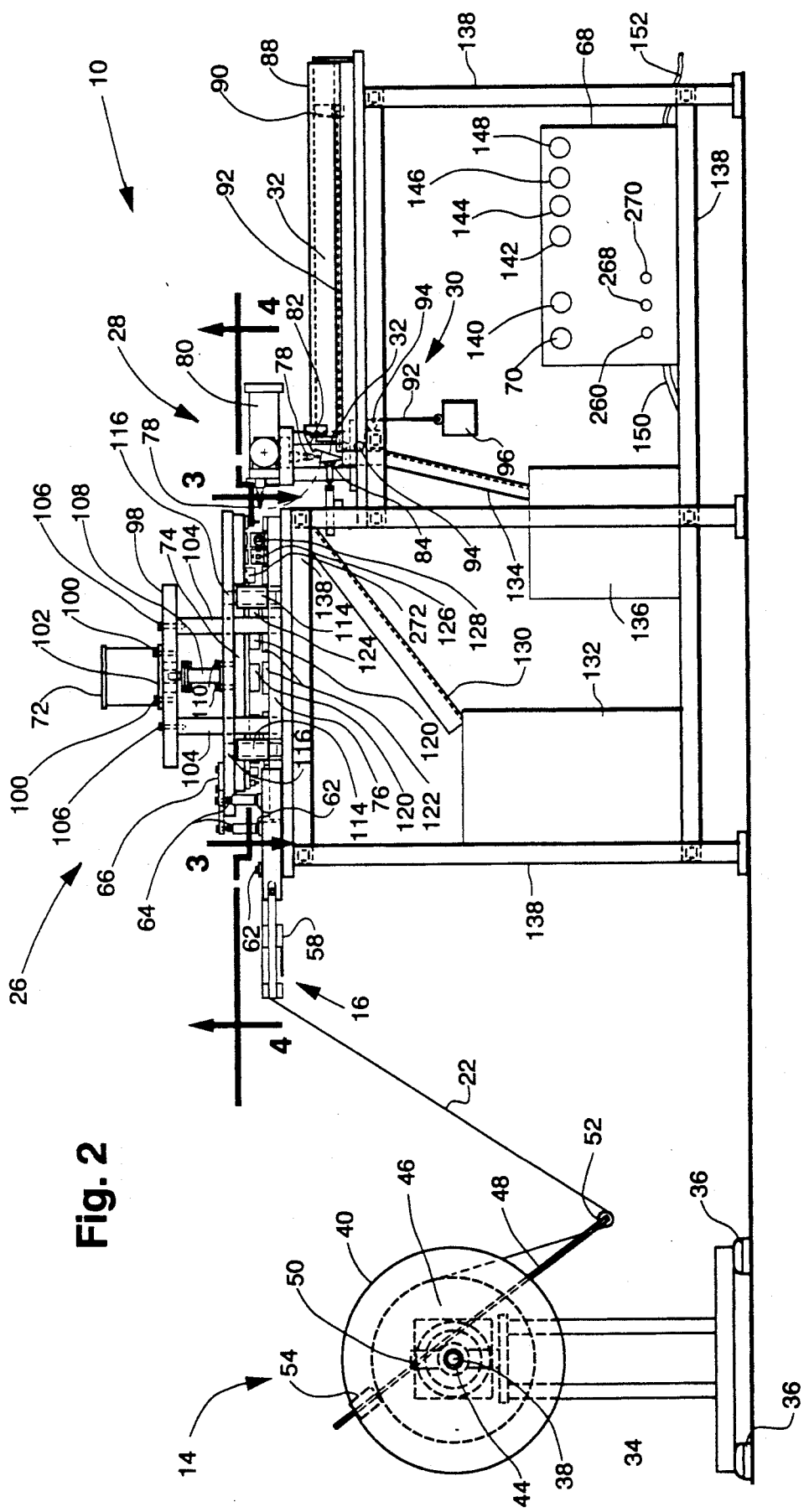
FIG. 2 is a simplified side elevation view of the machine as shown in FIG. 1.

The material webs 22 and 24 pay out from their respective infeed roll stands 14 and 18 into the web indexing infeeds 16 and 20 which in timed operational machine 10 cycles engagably clamp and indexably advance the respective material webs 22 and 24 into the infeed material die punch and product assembly station 26. The respective web indexing infeeds 16 and 20 are structurally, mechanically, and operationally the same, differing only in physical size wherein the lens material web indexing infeed 16 is of one dimensional size and the two temple material web indexing infeeds 20 are of a smaller but respectively identical dimensional size. Operationally, the respective webs 22 and 24 are engaged and indexably advanced by the spaced web infeed clamps 58 on a cyclic basis, the spaced web infeed clamps 58 respectively being pneumatically operated each by a clamp cycling air cylinder 60, the respective web clamp 58 dwells and web engagement pressures being established by clamp switches 62 and the clamp switch adjustment screw 64 wherein said switches 62 are spaced to reciprocally engage the screw 64 to effect reciprocal operation of the clamp cycling air cylinder 60 through contact deflection of the clamp cylinder switch trigger 66, all of which is initiated upon machine 10 activation through the control panel 68 start cycle switch 70, wherein said control panel 68 and the related switch and machine 10 operational indicator signal light means associated therewith are not shown in FIG. 1 but are as illustrated in FIG. 2 to be hereinafter described in greater detail.

Following the machine 10 cyclic indexing infeed of webs 22 and 24 to the material die punch and product assembly station 26, the master cylinder 72 is triggered to cycle and reciprocally operate a vertical displacement and retraction of the punch holder platen 74 and cooperatively with the fixed die table 76 effect a concurrent simultaneous plurality of machine 10 functional operations including punching, creasing, folding, component assembly, ultrasonic welding, and finished protective spectacle 12 delivery to envelope packaging, wherein more detailed descriptions of the specific machine 10 operations as above recited will be discussed in greater detail on consideration of subsequent illustrative Figures hereinafter.

With each operational cycle of said machine 10 as outlined above, a sufficient charge of lens material web 22 and temple material web 24 is indexably infed to the material die punch and product assembly station 26 for conversion thereof to a single finished protective spectacle 12, and a single protective spectacle 12 is delivered from said material die punch and product assembly station 26 to the product pick-up and delivery station 28, which receives and delivers each protective spectacle 12 singly to the packaging station 30 for individual protective envelope 32 insertion.

The product pick-up and delivery station 28 consists of a set of pneumatically operated pick-up fingers 78 driven by the pneumatic pick-up finger cylinder complex 80 by which the pick-up fingers 78 clampably engage a completed protective spectacle 12, and then pivotally rotate the same 90-degrees downward by said cylinder complex 80 to insertably deliver the spectacle 12 to an opened protective envelope 32 as shown in phantom, wherein one side of the open end of the envelope 32 is held by a set of retaining fingers 82 while the other side is held and pulled away by a pneumatic sucking cup 84 to thereby open and then hold open a protective envelope 32 for finished protective spectacle 12 insertion therein.

The packaging station 30 further includes an envelope feeding magazine 88 in which protective envelopes 32 are placed and retained for feeding to the product pick-up and delivery station 28, wherein said envelope feeding magazine 88 is operable by means of a simple gravity feed comprised of an envelope pusher 90 that is connected by a cable 92 about pulleys 94 to a depending weight 96 and is thereby caused to maintain a constant forward feed force on the protective envelopes 32 therein contained.

The machine 10 for automated manufacture of protective spectacles 12 as shown and illustrated in FIG. 1, and certain subsequent Figures hereinafter, may be constructed of metals or plastics, or any other suitable materials or combinations thereof.

Referring now to the side elevation view of said machine 10 as illustrated in FIG. 2, which is simplified in the respect that only the lens material infeed roll stand is shown, and not the temple material infeed roll stands 18, so as to reduce what would otherwise present clutter and confusion in the view at the material infeed end thereof. Additionally shown in FIG. 2 is side elevation detail of the infeed material die punch and product assembly station 26, and in particular the master cylinder 72 and the assembly thereof to reciprocally drive the punch holder platen 74. As shown, the master cylinder 72 is assembled to the master cylinder mounting and support base 98 by means of cylinder connecting bolts 100 threadably inserted through openings in the cylinder mounting base plate 102 and into cooperative threaded openings in said support base 98. The master cylinder mounting and support base 98 is in turn supportably assembled to the cylinder elevating posts 104 by post connecting bolts 106 so as to thereby elevate said master cylinder 72 sufficiently and thus enable vertical displacement and retraction of the master cylinder ram 108 in reciprocally driving the punch holder platen 74 to which it is connected by ram collar bolts 110. As the punch holder platen 74 is reciprocally displaced by the advance and retraction of the master cylinder ram 108, the punch holder platen 74 is maintained in close register and alignment by means of the punch holder platen register posts 114 having register lugs 116 which provide mechanically cooperative close tolerance clearance within the punch holder platen register openings 118 to thereby maintain said punch holder platen 74 in close and consistent alignment so the respective punches 120 carried thereby maintain operational register with the corresponding cooperative dies 122 during machine 10 production running.

As the material webs 22 and 24 are forwarded through the material die punch and product assembly station 26 and the spectacle product is formed and assembled, one of the operations performed is that of ultrasonic welding of a retaining tab over each inserted temple member, which is accomplished by a set of ultrasonic welding electrodes 124 as shown in FIG. 2. Following the ultrasonic welding station there are a set of earpiece fold-over pushers 126 and 128, one being for the left temple fold-over and the other for the right, afterwhich the protective spectacle 12 is then forwarded in a temple fold-over configuration to the product pick-up and delivery station 28.

As the material webs 22 and 24 are indexably advanced through the material die punch and product assembly station 26, the punch waste therefrom is advanced and discharged by gravity down the waste discharge chute 130 to be collected in the waste container 132 for removal and disposal. Similarly, the completed and envelope packaged protective spectacles 12 are released by the pneumatic sucking cup 84 and gravity deposited into the product discharge chute 134 for delivery thereby to the completed product collection box 136 and removal to counting, cartoning and either storage or shipping.

Also shown in greater detail in FIG. 2 are the interconnected horizonal and vertical members of the machine support frame 138, in addition to the machine stop switch 140 located in the control panel 68 in a position adjacent the start cycle switch 70, the later of which as was previously explained. Additional control panel switches include the machine reset switch 142 which is to reset the machine 10 for operational cycling during and after make-ready procedures, the fault reset switch 144 to react the machine 10 for operational cycling following a fault stoppage, the single cycle switch 146 to cycle said machine 10 through a single material infeed and product delivery cycle, and the single step switch 148 to cycle single step machine 10 functions through a single step cycle. The control panel 68 is electrically connected to the machine 10 operational stations through operational control conduit 150, and to a suitable power source through power connector conduit 152. The remaining control panel 68 positions are used for machine 10 malfunction indicator lights which will be explained in detail on consideration of the subsequent Figures hereinafter.

Figure 3:
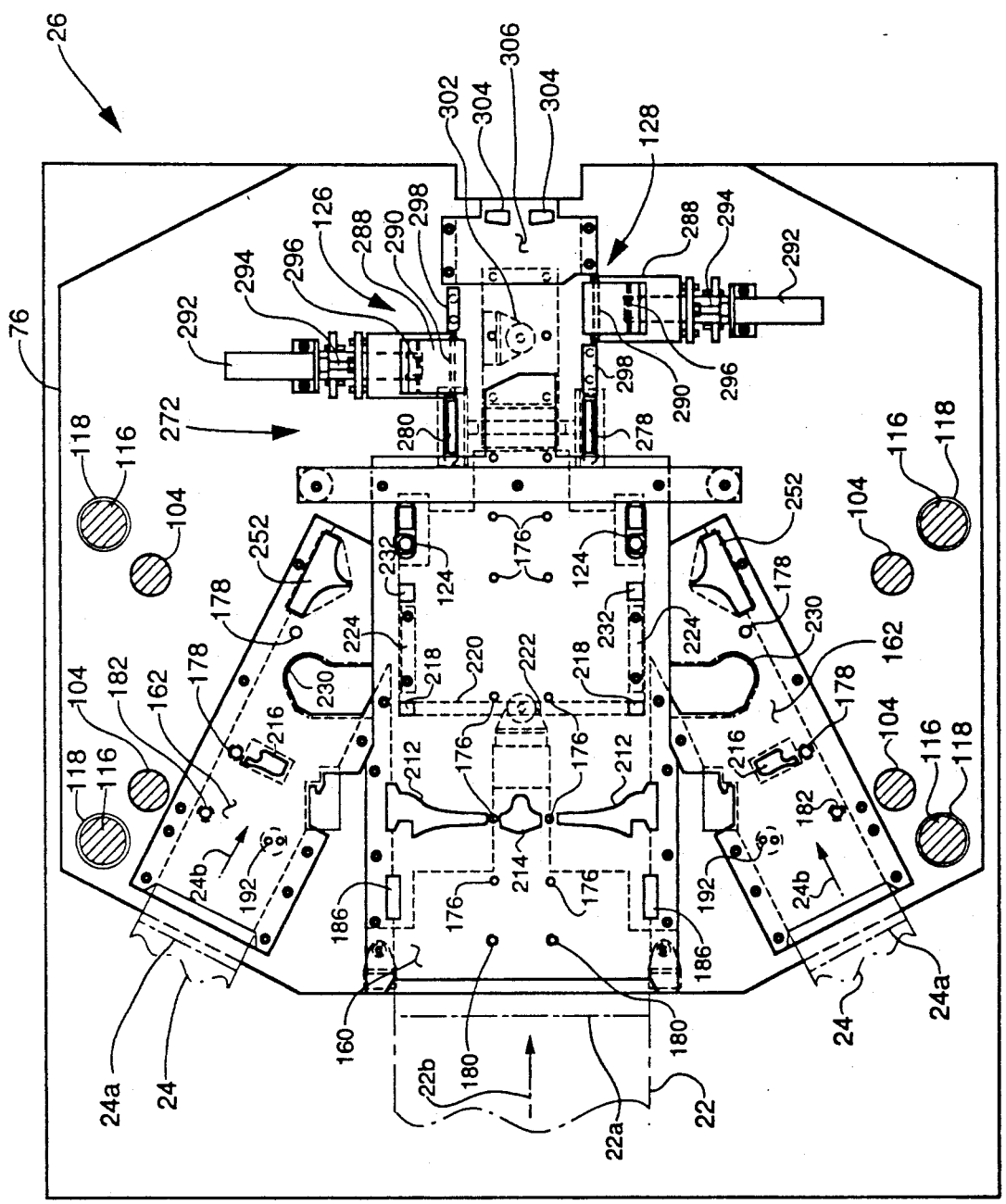
FIG. 3 is a top plan view of the die table section of said machine as shown in FIG. 2 and seen along the line 3—3 thereof.

Considering now the views shown in FIGS. 3, 4 and 5, which respectively illustrate the die table 76 of the infeed material die punch and product assembly station 26 of said machine 10, the punch holder platen 74 thereof, and in FIG. 5 results of the simultaneously performed functional operations progressively carried out by the mechanically cooperative die table 76 and punch holder platen 74 respectively upon the infeed lens material and temple material webs 22 and 24 during the indexable infeed cycling thereof through said station 26, which includes the concurrent plurality of punching, creasing, folding, component assembly, ultrasonic welding, and finished spectacle 12 delivery to envelope packaging as is hereinafter explained in further detail, and in so doing looking first at FIG. 5.

In FIG. 5, the lens material web 22 has a repetitively recycling imaginary infeed leading edge with every infeed on a machine 10 cycle, being designated as 22a and which is perpendicular to the direction of web 22 indexably infed cyclical advancement through the material die punch and product assembly station 26 as is indicated by arrow 22b, and the respective temple material webs 24 each likewise have a repetitively recycling imaginary infeed leading edge with every infeed on a machine 10 cycle, being designated as 24a and which is perpendicular to the directions of web 24 indexably infed cyclical advancements through said station 26. The geometrically shaped cross-hatched elements shown in FIG. 5 represent various punches of station 26 in relation to the material webs 22 and 24 as they are sequentially employed to form spectacle lens components 156 and the set of spectacle temple components 158 respectively therefor. As has been previously pointed out, all punches cycle simultaneously so that as the punch holder platen 74 as shown in FIG. 4, on cycling of the master cylinder 72 is advanced to cooperatively engage with the die table 76 as shown in FIG. 3, all operational functions are simultaneously performed upon the respective material infeed webs 22 and 24 and a single completed set of protective spectacles 12 is delivered from said machine 10 with each operational cycle thereof. However, for purposes of clarity, the production process will be sequentially described in terms of following the respective material infeed imaginary leading edges 22a and 24a through the series of indexing cycles from initial infeed to delivered product.

The material infeed webs 22 and 24 are advanced through the material die punch and product assembly station 26 at the die table 76 die face level, and in particular as shown in FIG. 3 in a mechanical disposition of being interposed between the respective die faces for webs 22 and 24 and cooperative overlying stripper plates 160 and 162 having complementary die opening cut-outs therein which function as a mechanical means whereby on each machine 10 cycle as the punches are retractably withdrawn therethrough they are cleaned of any adhereing lens or temple punch blank material so as to avoid machine 10 operational jams which might otherwise be resultant from punch blank material from either source hanging up on the punches.

The first die punch impression to be made in the material webs 22 and 24 on indexed infeed advancement of the respective imaginary infeed leading edges 22a and 24a are those of the lens material web register holes 164 made by the lens material web register hole punches 166 and the temple material web register holes 168 made by the temple material web register hole punches 170, which register holes 164 and 168 respectively serve during subsequent machine 10 cycles and continued infeed material advancement to receive either the lens material web register pins 172 or temple material web register pins 174 whereby webs 22 and 24 are positively maintained and held in operational alignment and register for subsequent sequential punching, creasing, folding, component assembly, ultrasonic welding, and completed spectacle 12 separation from the lens material web 22. As shown in FIG. 3, the respective stripper plates 160 and 162 of the die table 76 are provided with openings for the lens and temple web register pins 172 and 174 to pass through on machine 10 operational cycling and advancement of the punch holder platen 74 to the die table 76, being the lens material web register pin openings 176 and the temple material web register pin openings 178, as well as also openings for passage of the lens material web register hole punches 166 and the temple material web register hole punches 170, being respectively the lens material web register hole punch opening 180 and the temple material web register hole punch opening 182.

In mechanically accomplishing the processing operations herein taught, the lens web material being typically a plastic substance and less susceptable to the effects of ambient operational temperature and humidity conditions than is that of the temple web material which is typically a paper based product, is employed as the control web for purposes of primary machine 10 set and material guidance for automated assembly and fabrication of the protective spectacle 12 product. For the foregoing reason, and since uniform lens web material cross-web lateral dimension is important in the foregoing respect, the lens material web 22 is trimmed from both lateral sides thereof by the lens material lateral dimension uniforming punches 184 as shown in FIG. 5, which are accommodated in passage through the stripper plate 160 to the die table 76 by lateral dimension uniforming punch openings 186 as is shown in FIG. 3.

The next punch impressions to be made in the temple material webs are those for the temple adjustment stops 188 as shown in FIG. 5, which are a set of half-moon shaped imprints that may be selectively employed by a user to adjust the temple 158 extension in accommodating fit to head size of the user. The foregoing imprints are made with the temple adjustment stop punches 190 as shown in FIG. 4, which are accommodated in passage through the stripper plate 162 to the die table 76 by temple adjustment stop punch openings 192.

Next the laterally dimensioned lens material web 22 is engaged along the indexably advanced imaginary infeed leading edge 22a thereof with a laterally spaced set of lens forming punches 196 and an intermediately spaced nose notch punch 198 which punches simultaneously form the bottom lens profile 200 of the preceding spectacle lens component 156 and the top lens profile 202 of the following spectacle lens component 156. At this time the tabs 204 are also formed as parts of the spectacle lens component 156 structure, which tabs are thereafter folded and secured in a manner to be hereinafter described whereby are provided mechanical means for securing the adjustable temples to the protective spectacles 12.

Concurrent with the foregoing punch forming operation the temple end forming punches 206 engage the respective temple material webs 24 and effect die cutting of the temple stop extension 208 as well as the end of the temple ear bow 210. It will be noted that the spectacle temple components 158 from this stage forward are progressively formed as the temple material webs 24 are indexably advanced, thus to incrementally remove material and thereby maintain maximum operational control over the temple components 158 while they are being formed and mechanically advanced in convergence to assembly connection with the spectacle lens component 156.

Each of the foregoing punches are provided with corresponding openings in the appropriate stripper plates 160 and 162, and in the case of the lens forming punch 196 and nose notch punch 198 respectively being the lens forming punch opening 212 and the nose notch punch opening 214 in the lens die cooperative overlying stripper plate 160, and in the case of the temple end forming punches 206 being the temple end forming punch openings 216 in the respective temple die cooperative overlying stripper plates 162.

As the lens material web 22 continues to be indexably advanced with each machine 10 cycle, the tabs 204 are engaged by the die table 76 tab folding dies 218 mounted upon the reciprocating die bar 220 which is operable by the die bar cylinder 222 all as shown in FIG. 3, and bent upwards at a 90-degree angle to the spectacle lens component 156 as shown at 204' in FIG. 5. On continued indexably advanced movement of the lens material web 22 the 90-degree upward bent tabs 204' move under the die table 76 tab hold-down shoes 224 as shown in FIG. 3 and are further bent over also as shown in FIG. 5 as 204".

During continued indexably advanced forwarding of the lens material web 22 as above described, the continually angularly inward forwarding convergence of the respective temple material webs 24 moves the spectacle temple component 158 temple stop extensions 208 into closer proximity with the spectacle lens component 156 bent over tabs 204", whereupon the temple bow extension punches 226 on cycling of the punch holder platen 74 move to form the temple bow extensions 228 immediately prepatory to assembly of the temple components 158 with the lens component 156. In operational mechanical cooperation with the die table 76, the temple bow extension punches communicate through the temple bow extension punch openings 230 as shown in FIG. 3.

As the respective right and left temple stop extensions 208 are moved into insertable communication with the bent over tabs 204" on their continued indexable forward transit under the tab hold-down shoes 224, and they emerge therefrom, said tabs 204" are engaged and compressed by the tab creasing dies 232 as shown in FIG. 3 to be thereby conformed into a flattened condition against the temple stop extensions 208. Concurrent therewith the temple back bow punch 234 makes an initial temple back bow cut 236 as shown in FIG. 5, leaving the temple back bow connecting web 238 as that remaining forward moving temple material guidance control by which to mechanically effect final insertable communication of the temple bow extensions 228 slidably within the now folded and creased tabs 240.

On continued indexable forwarding of the respective material webs 22 and 24 the temple bow extensions 228, guided and controlled by the temple back bow connecting webs 238 as shown in FIG. 5, are fully inserted from either side within the bent over tabs 240 which are engaged by the ultrasonic welding electrodes 124 as shown in FIGS. 2 through 4 to provide a welded seal 242 and thereby functionally and structurally assemble the respective spectacle temple components 158 to the spectacle lens component 156 by means of welded retaining tabs 244. Concurrent with the ultrasonic tab welding, the temple back bow punch 234 completes the final temple back bow cut 246 to thereby severably free the respective spectacle temple components 158 from the temple material webs 24, leaving continued forwarding of the assembled protective spectacle 248 to be carried and controlled by the nose notch connecting webs 250 of the lens material web 22 and the lens material web register pins 172 which insertably communicate through the lens material web register holes 164 remaining within the nose notch connecting webs 250. Also, on simultaneously completing the initial and final temple back bow cuts 236 and 246, the respective temple back bow punches 234 do so by insertably communicating through the corresponding complementary temple back bow punch openings 252 in the temple die cooperative overlying stripper plates 162 as shown in FIG. 3.

During indexably advanced transit of the respective material infeed webs 22 and 24 as previously described, any jamming or mis-feed condition respectively with regard thereto is detected by one of the sensors therefor and signaled by a light on the control panel 68 as shown in FIG. 2. The lens material web feed status is monitered and signaled by the lens material web feed sensor 256 which is mounted on the punch holder platen 74 as shown in FIG. 4, with the sensed lens material web 22 operational infeed condition being transmitted to the control panel 68 as shown in FIG. 2 by means of the lens material web feed sensor control panel connecting cable 258 to operate the lens material web feed sensor indicating light 260. Likewise, the right and left temple material web status are respectively monitered and signaled by the right and left temple material web feed sensors 262 and 264 also mounted on the punch holder platen 74, with the sensed temple material web 24 operational infeed conditions being transmitted to the control panel 68 by means of the temple material web feed sensor control panel connecting cables 266 to respectively operate the right and left temple web feed sensor indicating lights 268 and 270. In the event of a web infeed malfunction the power to operate said machine 10 is automatically cut off by way of a sensor signal through the control panel 68 and the malfunction location as detected by the appropriate sensor is thereon indicated by an illumination of the corresponding sensor indicating light.

The assembled protective spectacle 248 as previously identified and discussed on earlier consideration of FIG. 5 is now further forwarded on the next indexable advancement into the earpiece folding station 272, wherein the right and left earpieces 274 and 276 are respectively engaged by the right and left earpiece folding dies 278 and 280 and thereupon bent inward at 90-degree upward angles to the protective spectacle lens section 282. The 90-degree fold configuration of the right and left earpieces as performed at the earpiece folding station 272 is as shown in FIG. 5, and the earpiece folding station 272 and the right and left folding dies 278 and 280 thereof are shown in FIGS. 2 through 4.

The spectacles now enter left and right earpiece fold-over pushers 126 and 128 as shown in FIGS. 2 and 3 for finishing of the assembled protective spectacles 248 by a folding of the respective earpieces into the typical closed spectacle configuration 284 as shown in FIG. 5. Operationally, the respective earpiece fold-over pushers 126 and 128 are mechanically assisted by directed air blasts from the earpiece fold-over air nozzles 286 mounted upon the punch holder platen 74 as shown in FIG. 4, each of which nozzle directs a stream of air to impinge upon the corresponding 90-degree upright standing earpieces 274 and 276 and thereby deflect them slightly inward as a cooperative fold-over assist just prior to and during cycling of the respective earpiece fold-over pushers 126 and 128. As is best shown in FIG. 3, the fold-over pushers each consist of a pivotal fold-over plate 288 the lower end of which pivots about a plate pin 290 when the pivot plate cylinder 292 is cycled to extend the ram 294 which is in turn pivotally connected to said plate 288 the upper end thereof by a pintle assembly 296. Each fold-over pusher is further provided with a stop block 298 opposite thereto, against which the opposing side of the assembled spectacle 248 abuts during completion of the earpiece fold-over operation in delivering a closed spectacle configuration 284 for separation from the lens material web 22.

The last operation to be performed by the infeed material die punch and product assembly station 26 is that of separating the completed protective spectacle 12 for delivery to the pick-up fingers 78 as previously shown and explained on consideration of FIG. 2, and which is accomplished by removal of the nose notch connecting webs 250 by means of the nose notch connecting web punches 300 as shown in FIGS. 4 and 5, which punches 300 thereupon communicate through the nose notch connecting web punch openings 304 in the auxiliary stripper plate 306 and by which said nose notch connecting webs 250 are removed to thereby deliver a completed protective spectacle 12 with each cycle of said machine 10, wherein the packaging sequence which thereafter follows is as was previously explained on the earlier detailed descriptive consideration of FIGS. 1 and 2.

The last illustration for consideration is that as shown in FIG. 5A, which is simply an opened protective spectacle 12 profile, being included herein for purposes of clearly depicting the various component parts as previously described during the fabrication thereof on indexable production transit of the material webs 22 and 24 through the infeed material die punch and product assembly station.

Although the invention herein disclosed has been shown and described in what is considered to be the most practical and preferred method and mechanical embodiment for the practice thereof, it is recognized that departures may be made therefrom within the scope thereof, which is not to be limited to the specific details disclosed herein but is to be accorded the full scope of the claims so as to embrace any and all equivalent methods and means.

We claim:

1. A machine for automated manufacturing of protective spectacles, said machine comprising in combination a lens material infeed roll stand for dispensing a web of lens material, a lens material web indexing infeed for effecting a cyclical indexable delivery of said web of lens material from said lens material infeed roll stand to a die punch and product assembly station, a set of temple material infeed roll stands for respectively dispensing a web of right and left temple material, a temple material web indexing infeed respectively for said webs of right and left temple material each for effecting said cyclical indexable delivery of said webs of right and left temple material from said temple material infeed roll stands to said die punch and product assembly station a cooperative punch and die means in said die punch and product assembly station to concurrently effect automated die punch formation of a protective spectacle lens component and a right protective spectacle temple component and a left protective spectacle temple component, a joining means in said die punch and product assembly station to automatically assemble said right and left protective spectacle temple components to said protective spectacle lens component and produce an assembled protective spectacle an earpiece fold-over means to effect a right and a left earpiece fold-over of said assembled protective spectacle to provide a completed protective spectacle in a closed spectacle configuration, and a die punch means to separate a completed protective spectacle from said lens material web and deliver the same in said closed spectacle configuration with each indexable cycle of said machine for automated pick-up and envelope packaging thereof.

2. A machine for automated manufacturing of protective spectacles according to claim 1 wherein said lens material infeed roll stand is provided with a lens material web tensioning means.

3. A machine for automated manufacturing of protective spectacles according to claim 1 wherein said temple material infeed roll stands are each provided with a temple material web tensioning means.

4. A machine for automated manufacturing of protective spectacles according to claim 1 wherein said joining means for automatically assembling said right and left protective spectacle temple components to said protective spectacle lens component is a spaced set of ultrasonic welding electrodes.

5. A method for automatically manufacturing protective spectacles said method comprising the steps of indexably infeeding from a plurality of roll stands respectively therefor a web of plastic lens material and simultaneous therewith indexably infeeding a web of right temple material and a web of left temple material to a die punch and product assembly station, cycling said die punch and product assembly station to simultaneously effect die punching of said web of plastic lens material and said webs of right and left temple material indexably infed thereto to automatically produce a protective spectacle lens component and a right protective spectacle temple component and a left protective spectacle temple component, forming assembled protective spectacles by automatically inserting said right and left temple components respectively within a set of bent over tabs formed in the plastic lens material of said protective spectacle lens component and thereafter effecting slidable joining of said temple components thereto by an automated ultrasonic welding of tab seals and automatically effecting simultaneously a right and a left earpiece fold-over of said assembled protective spectacles to thereby deliver a completed protective spectacle in a closed spectacle configuration.

* * * * *